(12) United States Patent
Flachbart

(10) Patent No.: US 7,195,610 B1
(45) Date of Patent: Mar. 27, 2007

(54) PNEUMATIC SYRINGE DRIVER

(75) Inventor: Eric J. Flachbart, East Burke, VT (US)

(73) Assignee: Cardinal Health 303, Inc., San Diego, CA (US)

( * ) Notice: Subject to any disclaimer, the term of this patent is extended or adjusted under 35 U.S.C. 154(b) by 561 days.

(21) Appl. No.: 10/245,793

(22) Filed: Sep. 17, 2002

Related U.S. Application Data

(60) Provisional application No. 60/322,832, filed on Sep. 17, 2001.

(51) Int. Cl.
*A61M 29/00* (2006.01)
*A61M 5/30* (2006.01)

(52) U.S. Cl. ..................... 604/99.01; 604/70

(58) Field of Classification Search ............ 604/68–70, 604/72, 97.01, 97.02, 140, 141, 97.03, 143, 604/98.01, 99.01, 99.02, 96.01, 99.03, 208, 604/145–147; 128/DIG. 1

See application file for complete search history.

(56) References Cited

U.S. PATENT DOCUMENTS 5,064,413 A * 11/1991 McKinnon et al. ........... 604/70
5,449,345 A * 9/1995 Taylor et al. .......... 604/100.03

* cited by examiner

*Primary Examiner*—Nick Lucchesi
*Assistant Examiner*—Matthew F. DeSanto
(74) *Attorney, Agent, or Firm*—Fulwider Patton LLP

(57) ABSTRACT

A pneumatic syringe driver having a control module for regulating pressure applied to the plunger of an associated syringe is disclosed. The syringe driver is adapted for receiving a compressed gas canister and for enabling the selective release of gas from the canister into a chamber, one wall of which being formed by the syringe plunger via a three-way valve. The valve also enables the selective venting of gas from the canister into the atmosphere, thereby forming a venturi which reduces the pressure in the chamber and causes the syringe plunger to be withdrawn into the chamber. A pressure sensor in communication with the control module is provided for pressure feedback. Pushbuttons or switches in communication with the control module are provided for defining the syringe driver operation. The device is suited for the selective inflation and deflation of a balloon attached to the syringe driver for a balloon angioplasty procedures.

14 Claims, 3 Drawing Sheets

PNEUMATIC SYRINGE DRIVER

CROSS REFERENCE TO RELATED APPLICATIONS

This patent applications claims priority of U.S. Provisional Patent Application No. 60/322,832, filed Sep. 17, 2001.

STATEMENT REGARDING FEDERALLY SPONSORED RESEARCH OR DEVELOPMENT

N/A

BACKGROUND OF THE INVENTION

While devices have been developed for automatic control over syringe actuation, the size and power requirements of such devices suggest against their use in environments in which space is limited or external power is not readily available. Such devices have been employed for balloon inflation in various surgical procedures including the opening of strictures, or narrowings of bodily passages, such as in endoscopic dilation where a balloon is used to open an esophageal stricture. Another application is in balloon angioplasty. For example, such applications involve the use of a syringe for delivering pressurized fluid for inflating a balloon. However, in surgical settings, there tends to be minimal free space immediately proximate the surgical site, thus rendering large and complex syringe actuation devices inappropriate. Furthermore, the cost and complexity of such automatic devices make them appropriate for sequential, repeated use. Repeated use requires that the devices be cleaned, serviced, and periodically recalibrated, resulting in higher operating costs.

Without such devices, precise control over fluid dispensed from a syringe has typically required the manual manipulation of a syringe plunger by an operator. For example, a physician may apply axial pressure on a syringe plunger to force pressurized fluid into an attached balloon for inflation. Other mechanical interfaces have been proposed for coupling operator movements to the syringe piston. One example of such interfaces includes the use of threads between the plunger and the syringe barrel whereby rotation of the plunger results in a gradual axial progression (or regression) of the plunger. Reliance on human operation exposes the inflation or deflation procedure to significant variability in terms of total volume of pressure fluid dispensed, rate at which the fluid is dispensed, and susceptibility to drawback.

Consequently, there is a need for a compact and inexpensive device which can accurately control the dispensing of fluid from a syringe, particularly for balloon angioplasty applications. The compact size of the device would make it suitable for use in space-limited environments, while the lower cost would enhance its suitability for one-time or disposable use.

BRIEF SUMMARY OF THE INVENTION

The presently disclosed invention pertains to a pneumatic syringe driver having a control module for regulating pressure applied to the piston of an associated syringe. The syringe driver is also adapted for receiving a canister of compressed gas such as carbon dioxide. A valve mechanism and conduits are provided in the driver for enabling the selective release of gas from the canister into a chamber, one wall of which being formed by the syringe piston. The valve mechanism and conduits also enable the selective venting of gas from the canister into the atmosphere, thereby forming a venturi which reduces the pressure in the chamber and causes the syringe piston to be withdrawn into the chamber.

An on-board battery is provided for powering the control module and the valve mechanism. A pressure sensor in communication with the control module is provided in the syringe for feedback purposes. Visual display or indicator elements are also provided in various embodiments of the invention for conveying status relative to syringe internal pressure, battery life, and/or other pertinent device information. Input elements such as pushbuttons or switches are in communication with the control module for defining the operation of the syringe driver.

One particular application of the disclosed device is for selectively inflating and deflating a balloon attached to the syringe driver in a balloon angioplasty procedure. The balloon may be attached directly or indirectly to the syringe driver.

BRIEF DESCRIPTION OF THE SEVERAL VIEWS OF THE DRAWING

These and other objects of the presently disclosed invention will be more fully understood by reference to the following drawing, of which.

DETAILED DESCRIPTION OF THE INVENTION

Figure 1:
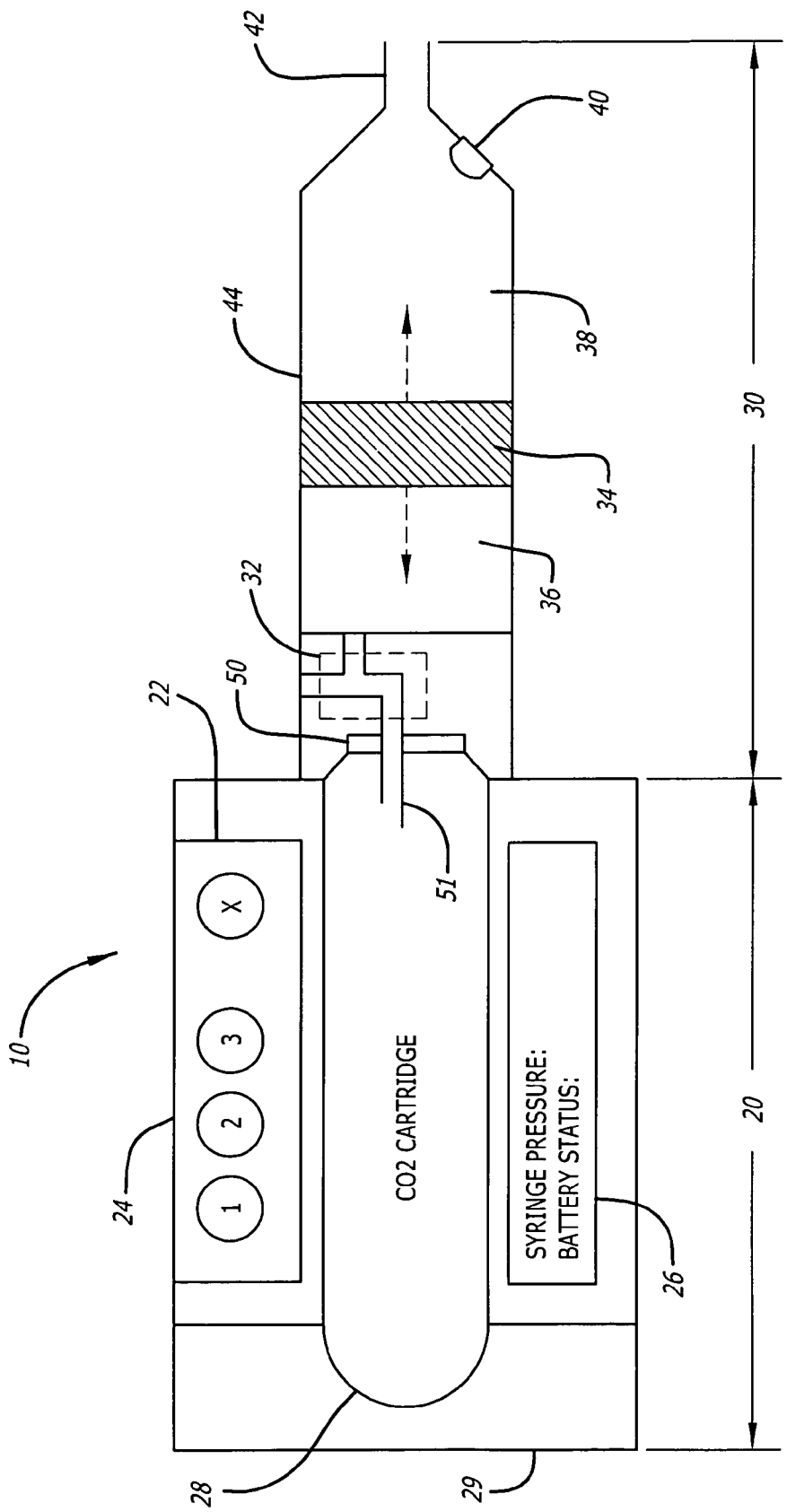
FIG. 1 is a diagrammatic view of components of a pneumatic syringe driver according to the presently disclosed invention.

A first embodiment of the presently disclosed pneumatic syringe driver 10 is illustrated in FIG. 1. The device is comprised of two main portions, a control and gas canister portion 20 and a valve and syringe portion 30.

The control and gas canister portion 20 includes a control module 22, an operator input interface 24, an operator output interface 26, a battery compartment (not shown), and a gas canister receptacle 28.

The control module 22 may comprise a custom integrated circuit or a digital signal processor or micro-controller with an associated and custom-programmed memory. In communication with the control module 22 and three-way valve 32 is a battery (not shown). A variety of batteries may be employed depending upon the power requirements of the active elements of the driver 10. A small form factor is beneficial, however, due to the need for overall compactness. In an alternative embodiment, a power port is provided on the driver 10 for interfacing a remote power supply to the control module 22 and the electronic three-way valve 32.

The operator input interface 24 comprises pushbuttons or switches and enables the operator to have one of several inflation routines executed by the control module 22 or to program a specific inflation regimen. The control module may respond immediately to each activation of an operator interface element, or may accumulate commands prior to be instructed to execute a programmed routine. Controls may be provided for commanding various degrees of balloon inflation, balloon inflation rate, and/or time delay between operations. Controls may also be provided for deflating the balloon according to the variables described above. In view of the applicability of the syringe driver 10 in surgical environments, it is preferred that the control interface elements be sealed and large enough to be actuated by gloved fingers.

The operator output interface 26 may comprise optical indicators such as light emitting diodes each have a pre-defined meaning. Alternatively, the output interface 26 may be comprised of a display screen, such as illustrated in FIG. 1. Various messages may be provided to an operator, including algorithm steps programmed, current programmed pressure, measured syringe pressure, projected gas pressure remaining, battery life, etc.

In a further embodiment, an electrical interface may be provided on the surface of the driver 10 and in communication with the control module for the purpose of enabling the remote programming of the inflation and deflation regimen, as well as the transmission of performance and status information to a remote terminal.

The control and gas canister portion 20 is provided in a first embodiment with a pre-installed gas canister which ahs a pierceable seal 50. In this embodiment, an element such as a threaded cap 29 is used to thrust the canister into communication with a fluid conduit 51 that pierces the canister seal. In a second embodiment with a pre-installed gas canister, the canister is already in fluid communication with the fluid conduit. In a third embodiment, the syringe driver is provided without the gas canister, and an access element such as the threaded cap 29 enables canister installation. Once again, tightening the cap 29 results in the fluid conduit piercing the canister seal.

The valve and syringe portion 30 comprises an electronic three-way valve 32 with associated fluid conduits, a syringe 44, a piston 34 dividing the syringe into a piston chamber 36 and a syringe chamber 38, a pressure sensor 40, and a balloon interface 42.

In one embodiment of the syringe driver of the present disclosure, the three-way valve 32 is an electronically driven rotary valve operating under the control of the control module 22. Alternatively, the valve may be provided as an electronically driven ball valve. Further still, the valve may be implemented through plural, independently displaceable shutters. Regardless of particular embodiment, a common requirement is that each port of the valve be gas-tight when closed.

One port of the three-way valve is in communication with the compressed gas canister once the canister is fully installed in the control and gas canister portion 20. As previously mentioned, this portion of the fluid conduit is preferably provided with a sharpened point or similar feature for piercing a seal in the compressed gas canister. A resilient seal such as an O-ring of rubber or like material may be provided in one embodiment for sealing a forward end of the gas canister to the valve and syringe portion 30 of the driver 10.

An anti-blow-by piston 34 is disposed for translation along the interior walls of the syringe 44. One side of the piston 34 forms part of the piston chamber 36, while another side of the piston 34 forms part of the syringe chamber 38. As gas pressure builds in the piston chamber relative to that in the syringe chamber, the piston moves in order to equalize the pressures. A sealing ring or rings (not shown) may also be used intermediate the piston and the syringe 44 barrel.

The syringe chamber 38 preferably contains incompressible fluid which, depending upon the specific application, may be liquid or gas. A pressure sensor 40 mounted within the syringe chamber 38 is in communication with the control module 22. Communication is preferably by way of sealed, electrically conductive wire (not shown).

While not illustrated in FIG. 1 for simplicity, the balloon interface 42 may include projections or other physical features which facilitate the attachment of a balloon to the syringe driver 10. Alternatively, the balloon interface 42 may be configured for use with a discrete fluid tube which is employed intermediate the balloon interface 42 and the balloon itself. The latter embodiment is particularly useful when the area surrounding a point of balloon insertion is limited or crowded with other surgical tools and instruments.

Figure 2:
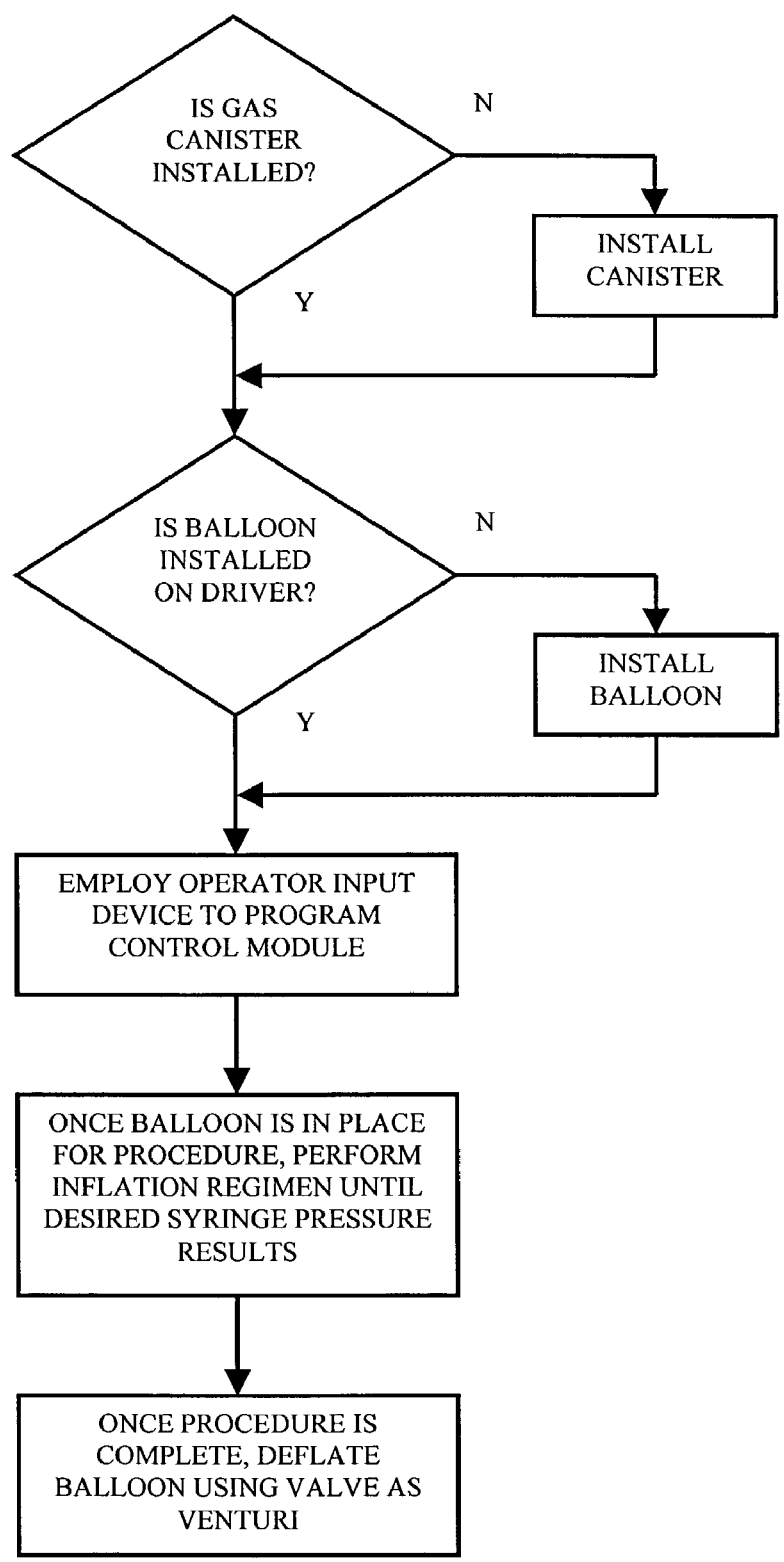
FIG. 2 is a flow chart illustrating a method of using the pneumatic syringe driver of FIG. 1.

The operation of the pneumatic syringe driver 10 is now described with reference to FIG. 2. If the syringe driver 10 is provided to a user with a gas canister 28 pre-installed, the user prepares the driver 10 for use by placing the gas canister 28 in fluid communication with the compressed gas canister port of the three-way valve 32, such as by tightening the threaded cap 29 against the canister 28. This action causes a seal enclosing the canister to be pierced and places the canister contents in fluid communication with the valve 32.

Alternatively, if the pneumatic syringe driver 10 is provided to the user without a pre-installed compressed gas canister 28, such a canister is inserted and placed in fluid communication with the canister port of the three-way valve, such as in the manner just described.

If a balloon has not already been attached to the balloon interface 42 of the syringe driver, one is now attached, and the balloon is disposed in position for inflation as required. Alternatively, the balloon is disposed in the operating environment prior to it being attached to the syringe driver.

Through use of the operator input interface 24, a user such as a surgeon can program the device to inflate the balloon according to a desired regimen. Then, once the driver and balloon are placed in the proper position and other surgical procedures have occurred or are ready to be performed, the inflation regimen can be started.

Figure 3A:
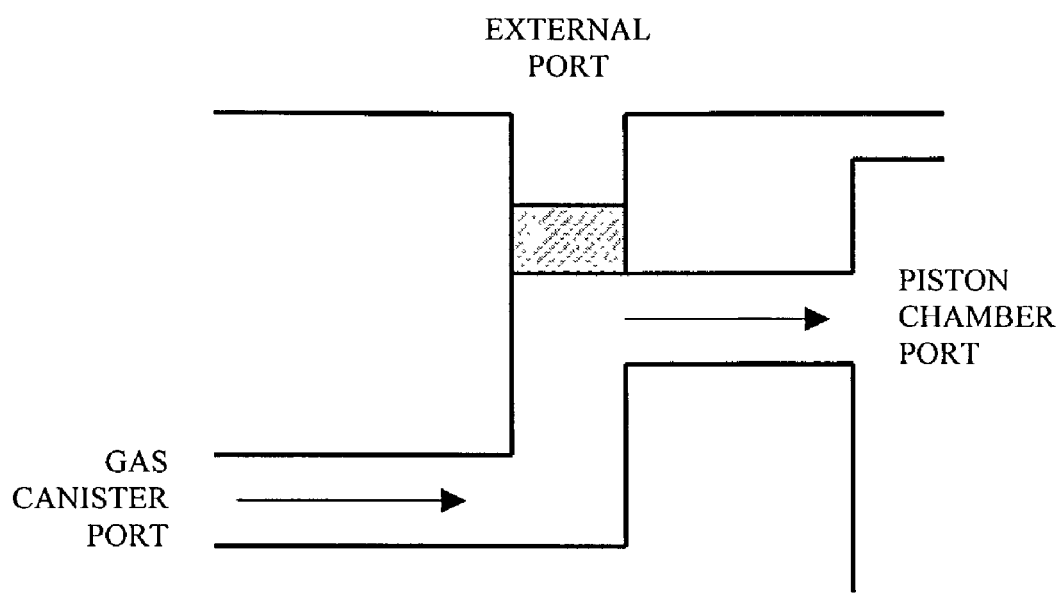
FIGS. 3A and 3B illustrate the configuration of a three-way valve of the pneumatic syringe driver of FIG. 1 during various modes of operation.

Inflation of the balloon occurs when the control module 22 commands the three-way valve 32 to open a fluid path from the gas canister 28 to the piston chamber 36 (FIG. 3A). This pathway is maintained until the pressure sensor 40 detects a target pressure reading in the syringe chamber 38. As gas flows from the gas canister 28 into the piston chamber 36, the piston chamber pressure will rise, resulting in the piston 34 being urged into the syringe chamber 38 and increasing the pressure in the balloon inflation fluid. Syringe chamber pressure may thus be one of the parameters programmed into the control module 22 via the operator input interface 24. Once the proper pressure is achieved in the syringe chamber 38, the three-way valve 32 is commanded by the control module 22 to close the fluid pathway.

Additional sequences of pressure increase in the piston chamber 36 may be affected by operation of the three-way valve until the desired balloon inflation is achieved.

Once the surgical procedure requiring balloon inflation has been completed, a certain portion of the inflation fluid pressure may be relieved by opening a fluid pathway between the piston chamber 36 and the atmosphere via the three-way valve 32. However, there may still be sufficient pressure in the syringe chamber 38 to prevent complete deflation of the balloon.

Figure 3B:
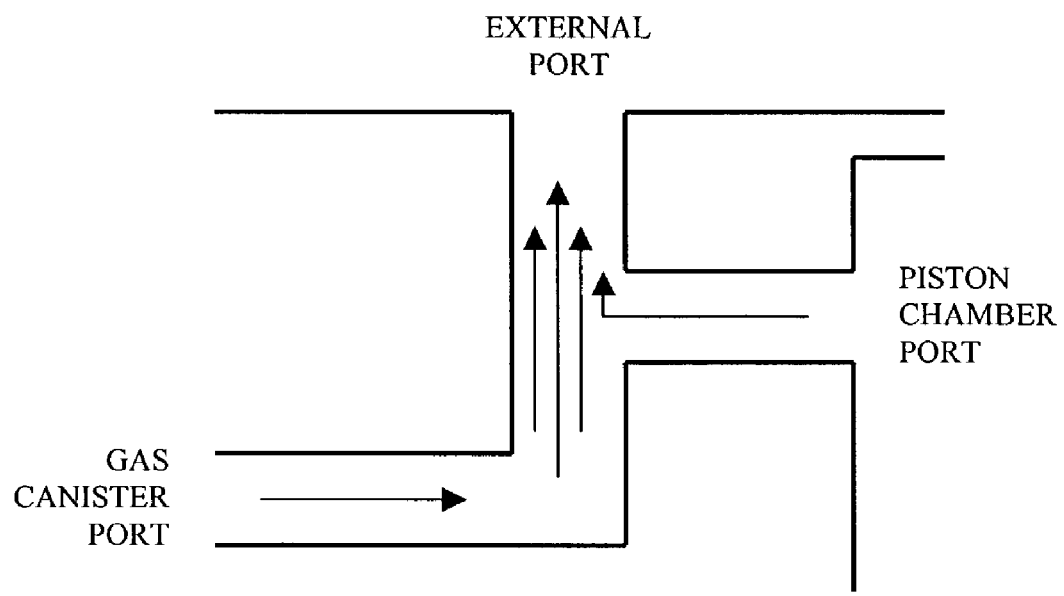

To further reduce the syringe chamber 38 pressure, all three ports of the three-way valve 32 may be placed in mutual communication by the control module 22, as in FIG. 3B. This will result in a flow of gas from the canister to the atmosphere, thus creating a venturi with respect to the piston chamber 36. As the compressed gas flows rapidly through the three-way valve towards the exterior port, the pressure within the valve decreases in accordance with the Bernoulli effect. This results in a flow of gas from the piston chamber into the valve and consequently the retraction of the piston 34 out of the syringe chamber 38. The pressure in the syringe chamber 38 thereby decreases, and the attached balloon is further deflated. The control module may monitor the pressure within the syringe chamber 38 via the pressure sensor 40 in controlling the three-way valve 32. The balloon may then be removed from its operating site.

The gas canister 28 is provided with enough pressurized gas to carry out the foregoing inflation regimen, including instances in which the attached balloon is inflated and deflated multiple times during a procedure. However, in order to minimize the size of the pneumatic syringe driver, only enough gas is provided to ensure operation for one procedure. The inexpensive electronics and battery power supply thus make the disclosed device ideal for single, disposable use.

These and other examples of the invention illustrated and described above are intended by way of example and the actual scope of the invention is to be limited solely by the scope and spirit of the following claims.

What is claimed is:

1. A pneumatic syringe driver comprising:
    an internal power source;
    a control module in communication with the power source;
    a three-way valve in communication with and operative under the control of the control module, the valve having a first port in fluid communication with a first fluid conduit, a second port in fluid communication with a second fluid conduit, and a third port in fluid communication with a third fluid conduit, the first port of the three-way valve being in communication with the atmosphere through the first fluid conduit, wherein the three-way valve is an electronic valve and operates under the control of the control module;
    a compressed gas canister in fluid communication through the second fluid conduit with the second port of the three-way valve;
    a syringe having a balloon interface for mechanically communicating with a balloon disposed thereon;
    a piston disposed for axial movement along the length or the syringe and dividing the syringe into a piston chamber and a syringe chamber,
    wherein the piston chamber is in fluid communication with the third port of the three-way valve through the third fluid conduit; and
    wherein the three-way valve may be controlled by the control module to have a first actuation state and a second actuation state, the first actuation state allowing gas to flow from the compressed gas canister through the second fluid conduit into the second port of the three-way valve and through the third port of the three-way valve into the third fluid conduit and into the piston chamber, and the second actuation state allowing gas to flow from the piston chamber through the third fluid conduit and third port of the three-way valve into the three-way valve and then through the first port of the three-way valve and first fluid conduit to the atmosphere.

2. The syringe driver of claim 1, further comprising a pressure sensor for detecting fluid pressure within the syringe chamber and for communicating the detected pressure to the control module.

3. The syringe driver of claim 2, wherein the control module is responsive to the detected pressure from the pressure sensor in controlling the three-way valve.

4. The syringe driver of claim 1, wherein the syringe and piston have a substantially circular cross-section.

5. The syringe driver of claim 4, wherein the piston further comprises at least one resilient seal about a circumferential surface thereof and in communication with an interior surface of the syringe.

6. The syringe driver of claim 1, wherein the internal power source is a battery.

7. The syringe driver of claim 1, wherein the control module is selected from the group consisting of a custom integrated circuit, a digital signal processor, and a programmed micro-controller.

8. The syringe driver of claim 1, wherein the second port of the three-way valve comprises a piercing member for piercing a seal in the gas canister when the gas canister is installed in the syringe driver.

9. The syringe driver of claim 1, wherein the compressed gas canister contains compressed carbon dioxide.

10. The syringe driver of claim 1, further comprising an operator input interface in communication with the control module for programming an operating regimen to be executed by the control module.

11. The syringe driver of claim 1, further comprising an operator output interface for selectively conveying syringe driver operating characteristics to an operator in visual form.

12. The syringe driver of claim 1, wherein when the three-way valve further has a third actuation state, the third actuating state allowing gas to flow from the compressed gas canister through the second fluid conduit and second port of the three-way valve through the three-way valve and out through the first port and first fluid conduit to the atmosphere, and also allowing gas to flow from the piston chamber through the third fluid conduit and third port of the three-way valve into the three-way valve and out through the first port of the three-way valve and first fluid conduit to the atmosphere.

13. A method of operating a pneumatic syringe driver for selectively inflating the interior of a balloon in fluid communication therewith, the syringe driver comprising a control module with associated power supply, an operator input interface in communication with the control module for enabling the programming of the operation of the control module, a compressed gas canister, a syringe having a fluid-tight piston disposed therein, the interior of the syringe being divided into a piston chamber on one side of the piston and a syringe chamber on the other side of the piston, and a three-way valve having a first port in fluid communication with the gas canister, a second port in fluid communication with the atmosphere external to the syringe driver, and a third port in fluid communication with the piston chamber, the method comprising:
    programming an operating regimen into the control module through the use of the operator input interface;
    controlling the three-way valve to place the gas canister and piston chamber in fluid communication, whereby increasing pressure in the piston chamber forces the piston into the syringe chamber;
    controlling the three-way valve to prevent fluid flow between the three ports; and
    controlling the three-way valve to place all three ports in mutual fluid communication, whereby gas from the piston chamber is vented to the atmosphere and creates a venturi with respect to the piston chamber according to the Bernoulli effect as compressed gas from the gas canister vents to the atmosphere.

14. The method of claim 13, wherein the syringe driver further comprises a pressure sensor in communication with the control module for detecting the pressure within the syringe chamber, the method further comprising:

detecting a threshold pressure within the syringe chamber between the step of controlling the three-way valve to place the gas canister and the piston chamber in fluid communication and the step of controlling the three-way valve to prevent fluid flow between the three ports.

* * * * *